US008135137B2

(12) United States Patent
Ito

(10) Patent No.: US 8,135,137 B2
(45) Date of Patent: Mar. 13, 2012

(54) SOUND IMAGE LOCALIZATION APPARATUS

(75) Inventor: Gempo Ito, Kanagawa (JP)

(73) Assignee: Panasonic Corporation, Osaka (JP)

( * ) Notice: Subject to any disclaimer, the term of this patent is extended or adjusted under 35 U.S.C. 154(b) by 789 days.

(21) Appl. No.: 12/282,414

(22) PCT Filed: Mar. 12, 2007

(86) PCT No.: PCT/JP2007/054773

§ 371 (c)(1),
(2), (4) Date: Sep. 10, 2008

(87) PCT Pub. No.: WO2007/119330

PCT Pub. Date: Oct. 25, 2007

(65) Prior Publication Data

US 2009/0046865 A1 Feb. 19, 2009

(30) Foreign Application Priority Data

Mar. 13, 2006 (JP) ................................. 2006-067631

(51) Int. Cl.
*H04R 5/00* (2006.01)
*H04B 15/00* (2006.01)
*A61F 11/06* (2006.01)
*G10K 11/16* (2006.01)
*H03B 29/00* (2006.01)

(52) U.S. Cl. ......................... 381/17; 381/94.2; 381/71.1

(58) Field of Classification Search .................... 381/17, 381/71.1, 94.2, 94.1, 94.3
See application file for complete search history.

(56) References Cited

U.S. PATENT DOCUMENTS 5,404,406 A * 4/1995 Fuchigami et al. ............. 381/17
5,598,478 A * 1/1997 Tanaka et al. ................... 381/17
5,761,315 A * 6/1998 Iida et al. ........................ 381/18
7,451,006 B2 * 11/2008 Eid et al. ......................... 700/94
(Continued)

FOREIGN PATENT DOCUMENTS

WO 2004010412 A2 1/2004

OTHER PUBLICATIONS

Sincaglia, N.; Rebaud, S.; "Product Design Considerations for Implementing 3D Audio Algorithms within Existing Multichannel Formats", Proceedings of the 16th International Conference of the Audio Engineering Society, May 8-11, 2004, pp. 105-115, Berlin, Germany.

(Continued)

*Primary Examiner* — Hai Phan
(74) *Attorney, Agent, or Firm* — Pearne & Gordon LLP

(57) ABSTRACT

The present invention is to provide a sound image localization apparatus which can prevent the lowering of the amplitude of the sound image localizing signal, the occurrence of clipping, and deterioration of the sound image localization component of the sound image localizing signal. The sound image localization apparatus according to the present invention comprises a frequency component analyzing unit 104 which analyzes the frequency component obtained from the sound source signal, a frequency component analyzing unit 103 which analyzes the frequency component obtained from the head-related transfer function that corresponds to the target position, a frequency component comparing/correcting unit 105 which decides whether a clipping occurs from a particular frequency range by comparing the frequency component of the analyzed sound source signal with the frequency component of the head-related transfer function, and a sound image localization processing unit 106 which outputs to acoustic device, a sound image localizing signal whose amplitude component corresponding to a particular frequency range of the sound source signal or a head-related transfer function is suppressed when the frequency component comparing/correcting unit 105 determines that a clipping has occurred.

6 Claims, 22 Drawing Sheets

U.S. PATENT DOCUMENTS

| | | | | |
|---|---|---|---|---|
| 7,454,026 | B2 * | 11/2008 | Yamada | 381/310 |
| 7,676,047 | B2 * | 3/2010 | Aylward et al. | 381/97 |
| 2007/0165890 | A1 * | 7/2007 | Fusakawa et al. | 381/309 |
| 2009/0034772 | A1 * | 2/2009 | Iida et al. | 381/356 |
| 2010/0027799 | A1 * | 2/2010 | Romesburg et al. | 381/28 |

OTHER PUBLICATIONS

Supplemental European Search Report for Appl. EP 07738245 dated Jun. 14, 2010.

* cited by examiner

SOUND IMAGE LOCALIZATION APPARATUS

FIELD OF THE INVENTION

The present invention relates to a sound image localization apparatus for localizing a sound image in a given spot in three-dimensional space.

BACKGROUND OF THE INVENTION

As shown in FIG. 20, a conventional sound image localization apparatus includes a head-related transfer function storage unit 901 having head-related transfer functions corresponding to respective positions, a sound image being localized on the basis of a head-related transfer function corresponding to a designated position, a head-related transfer function selecting unit 902 for selecting a head-related transfer function corresponding to a designated position, and a sound image localization processing unit 903 for filtering a sound source signal on the basis of the selected head-related transfer function, and outputting a sound image localizing signal produced through a sound image localization process.

The sound source signal input into the above-mentioned sound image localization apparatus is convolved with a head-related transfer function corresponding to a designated position, and outputted to an acoustic device such as a headphone or speakers as a sound image localizing signal. When the sound image localizing signal is outputted to the acoustic device under the condition that the head-related transfer function H(f) exceeds 0 dB in the range of a peak included in its amplitude component as shown in FIG. 21, the sound image localizing signal may become distorted, and have a distortion called clipping.

In order to solve this problem, the conventional sound image localization apparatus reduces a gain on all frequency range, and utilizes the head-related transfer function which limits the peak frequency range not to exceed 0 dB as shown in FIG. 22. Also, other conventional sound image localization apparatus aims to prevent clipping on sound image localizing signal by applying sound volume compression methods commonly referred to as limiter or compressor.

As an example of a conventional sound processing apparatus, there has been known a circuit for controlling a quality of a sound to be outputted from an acoustic device such as speakers to prevent the sound from being distorted by a clipping distortion (see patent document 1).

Patent document 1: Japanese Public Patent Publication No. 07-059187

DISCLOSURE OF THE INVENTION

Problems to be Solved by the Invention

The above-mentioned conventional sound image localization apparatus however encounters such a problem that, when the sound source signal is processed on the basis of a head-related transfer function for holding down its peaks to 0 [dB] or less, the volume of a sound image localizing signal is considerably reduced in comparison with that of the sound source signal.

Further, a method using a limiter, a compressor or the like acts on a signal nonlinearly in the time domain to deteriorate an output signal's frequency characteristic. Therefore, the component necessary to form peaks and dips of the amplitude component of the head-related transfer function, and localize a sound image tends to be distorted.

Further, a sound processing apparatus, to which a sound volume and quality adjusting function disclosed in the patent document 1 is applied, is adapted to reduce peaks and dips of the amplitude component of the head-related transfer function. Therefore, the sound processing apparatus tends to deteriorate the component for localizing a sound image.

In order to solve the problems, the present invention is to provide a sound image localization apparatus which can suppress a clipping distortion without reducing the volume of the sound image localizing signal, and prevent its signal components necessary for localizing a sound image from being deteriorated.

Means for Solving the Problem

According to an aspect of the invention, a sound image localization apparatus for executing a sound image localizing processing on the basis of a head-related transfer function, comprising: a frequency component comparing/correcting unit operable to compare frequency components of a sound source signal with frequency components of the head-related transfer function corresponding to a position of the sound image to be localized, to determine whether or not a sound image localizing signal is distorted by a clipping distortion, and to correct the frequency components of the sound source signal or the head-related transfer function when the sound image localizing signal is distorted by the clipping distortion; and a sound image localization processing unit operable to execute data processing by using the sound source signal and the head-related transfer function corrected by the frequency component comparing/correcting unit, to output a sound image localizing signal, wherein the frequency component comparing/correcting unit suppresses an amplitude of the head-related transfer function for each unit of peak or dip.

In this aspect of the invention, when it is determined that the clipping occurs, an amplitude component is suppressed for each unit of peak or dip of the head-related transfer function, avoiding lowering the sound volume of the sound image localizing signal while avoiding the occurrence of the clipping and further avoiding deteriorating the component for positioning a sound image included in the sound image localizing signal.

According to another aspect of the invention, a sound image localization apparatus for executing a sound image localizing processing on the basis of a head-related transfer function, comprising: a sound image localization processing unit operable to process a sound source signal by using a head-related transfer function corresponding to a target position, to output a sound image localizing signal; and a frequency component comparing/correcting unit operable to determine whether or not the sound image localizing signal is distorted by a clipping distortion in a frequency range, and to correct frequency components of the sound image localizing signal when the sound image localizing signal is distorted by the clipping distortion in the frequency range, wherein the frequency component comparing/correcting unit suppresses an amplitude of the head-related transfer function for each unit of peak or dip.

In this aspect of the invention, when the clipping occurs, an amplitude component is suppressed for each unit of peak or dip of the head-related transfer function, avoiding lowering the sound volume of the sound image localizing signal while avoiding the occurrence of the clipping and further avoiding deteriorating the component for positioning a sound image included in the sound image localizing signal.

Advantageous Effect of the Invention

As described above, the present invention is to provide a sound image localization apparatus which can suppress a clipping distortion without reducing the volume of the sound image localizing signal, and prevent its signal components necessary for localizing a sound image from being deteriorated.

EXPLANATION OF THE REFERENCE NUMERALS

Figure 1:
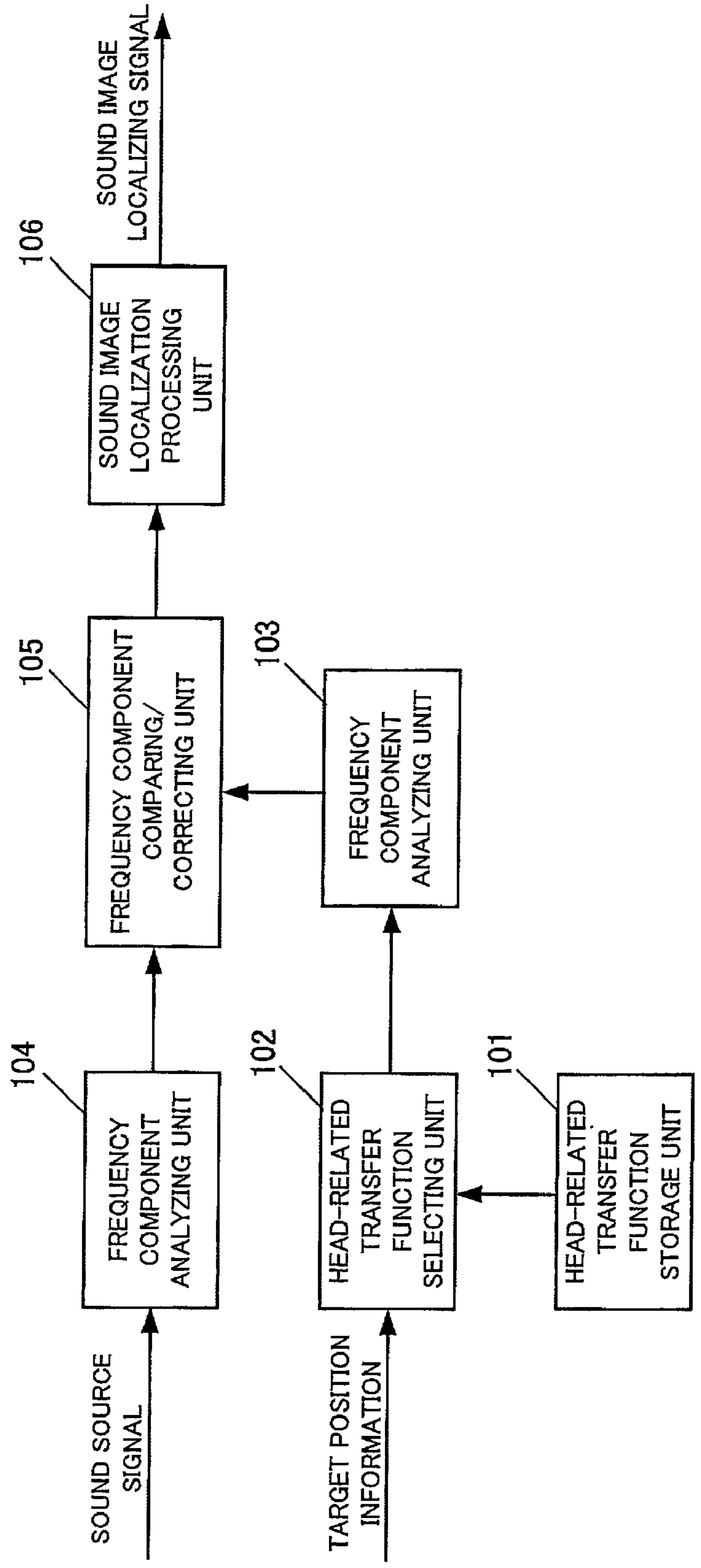
FIG. 1 is a block diagram showing a sound image localization apparatus according to the first embodiment of the present invention.

101: head-related transfer function storage unit
102: head-related transfer function selecting unit
103: frequency component analyzing unit
104: frequency component analyzing unit
105: frequency component comparing/correcting unit
106: sound image localization processing unit
111: head-related transfer function storage unit
112: head-related transfer function selecting unit
201: sound image localization processing unit
202: frequency component analyzing unit
203: frequency component correcting unit
211: sound image localization processing unit
901: head-related transfer function storage unit
902: head-related transfer function selecting unit
903: sound image localization processing unit

THE PREFERRED EMBODIMENTS OF THE PRESENT INVENTION

Embodiments of the sound image localization apparatus according to the present invention will be described with reference to the accompanying drawings.

First Embodiment

FIG. 1 is a block diagram showing a sound image localization apparatus according to the first embodiment of the present invention.

As shown in FIG. 1, the sound image localization apparatus comprises a head-related transfer function storage unit 101 having head-related transfer functions corresponding to respective positions to be selectively set as a target position, a sound image being localized on the basis of a head-related transfer function corresponding to a target position, a head-related transfer function selecting unit 102 operable to select a head-related transfer function corresponding to a target position, a frequency component analyzing unit 103 operable to analyze frequency components of the selected head-related transfer function, a frequency component analyzing unit 104 operable to analyze frequency components of a sound source signal, a frequency component comparing/correcting unit 105 operable to determine whether or not a sound image localizing signal is distorted by a clipping distortion, and to correct the frequency component of the head-related transfer function, if clipping occurs, and a sound image localization processing unit 106 operable to perform filtering based on the head-related transfer function and outputs the sound image localization signal that has been sound image localization-processed to the acoustics device such as headphones and speakers that are not shown in figures.

The head-related transfer function storage unit 101 has, as filter coefficients to be set to finite impulse response filter (hereinafter simply referred to as "FIR filter"), head-related transfer functions corresponding to respective positions to be selectively designated as a target position.

Figure 21:
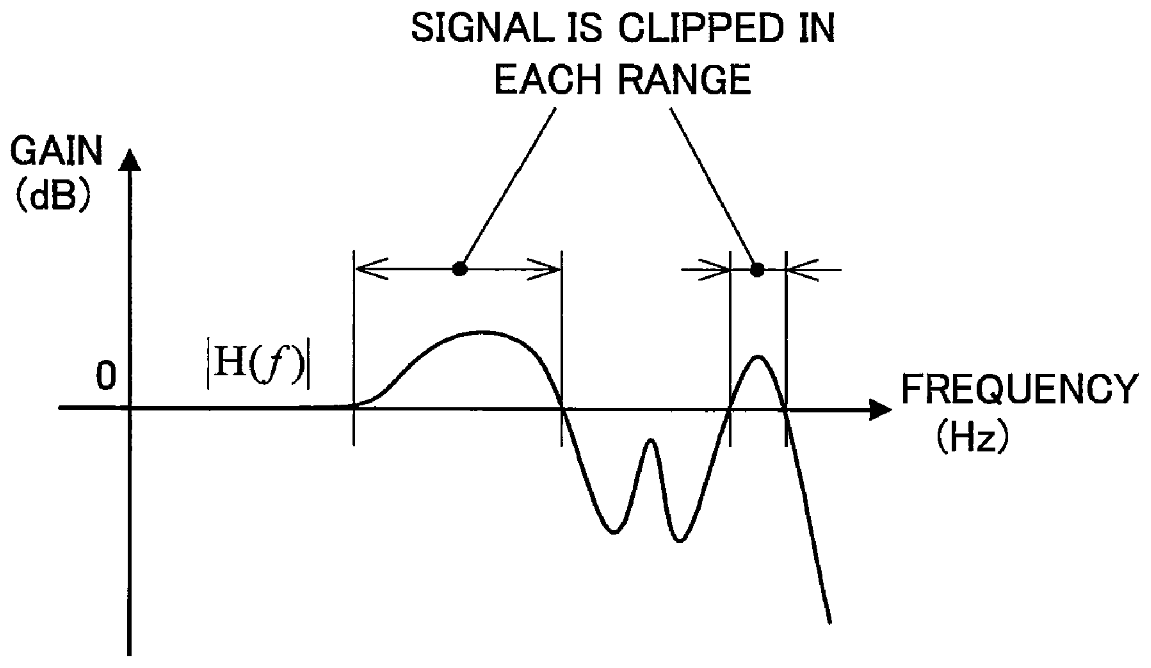
FIG. 21 is a diagram showing one example of head-related transfer function having the possibility to cause clipping distortion in frequency ranges.
Figure 22:
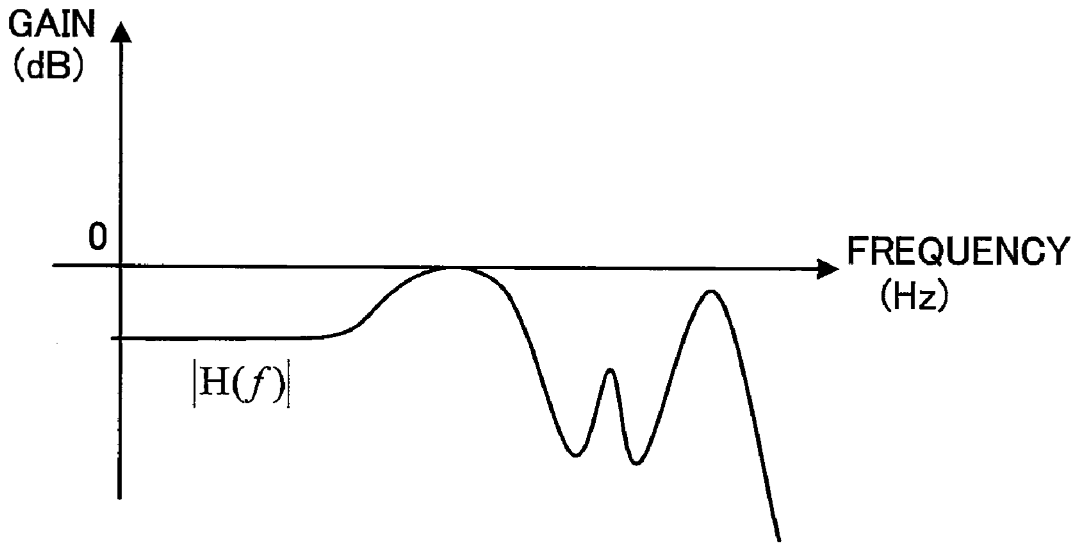
FIG. 22 is a diagram showing an example of head-related transfer function adjusted for reducing the clipping distortion.

Here, the head-related transfer function may be characterized in that the volume of the sound image localizing signal is not reduced in comparison with that of the original sound source signal when the sound source signal is convolved with the selected head-related transfer function stored in the head-related transfer function storage unit 101. In other words, the selected head-related transfer function may exceed 0 dB in a frequency range corresponding to its peak as shown in FIG. 21.

These elements of the sound image localization apparatus shown in FIG. 1 may be constituted by an integrated circuit. The sound image localization apparatus may be operated by a processor such as foe example a central processing unit (CPU). In this case, these elements of the sound image localization apparatus may be respectively realized as program modules.

The following description is directed to the operation of the sound image localization apparatus according to the first embodiment of the present invention.

Firstly, the head-related transfer function selecting unit 102 selects, from the head-related transfer function storage unit 101, a head-related transfer function corresponding to a target position set by position information, and outputs the selected head-related transfer function to the frequency component analyzing unit 103.

When, on the other hand, the head-related transfer function selecting unit 102 can not select, from the head-related transfer function storage unit 101, a head-related transfer function corresponding to a target position set by position information, the head-related transfer function selecting unit 102 may calculate a head-related transfer function corresponding to a target position set by position information by using two or more head-related transfer functions corresponding to positions adjacent to the designated target position, and by performing a well-known interpolating operation.

Next, the frequency component analyzing unit 103 converts a selected head-related transfer function into frequency components by using, for instance, Fourier transform, and outputs the frequency components of the selected head-related transfer function to the frequency component comparing/correcting unit 105.

Similarly, the frequency component analyzing unit 104 converts a sound source signal into frequency components by using, for instance, Fourier transform, and outputs the frequency components of the sound source signal to the frequency component comparing/correcting unit 105.

The frequency component comparing/correcting unit 105 determines whether the sound image localizing signal is distorted by a particular frequency range by comparing the frequency components of the selected head-related transfer function with the frequency components of the sound source signal. When the determination is made that the sound image localizing signal is distorted by the clipping distortion, frequency component comparing/correcting unit 105 corrects the frequency component of the head-related transfer function and, outputs the corrected frequency component of the head-related transfer function to the sound image localization processing unit 106.

Figure 2:
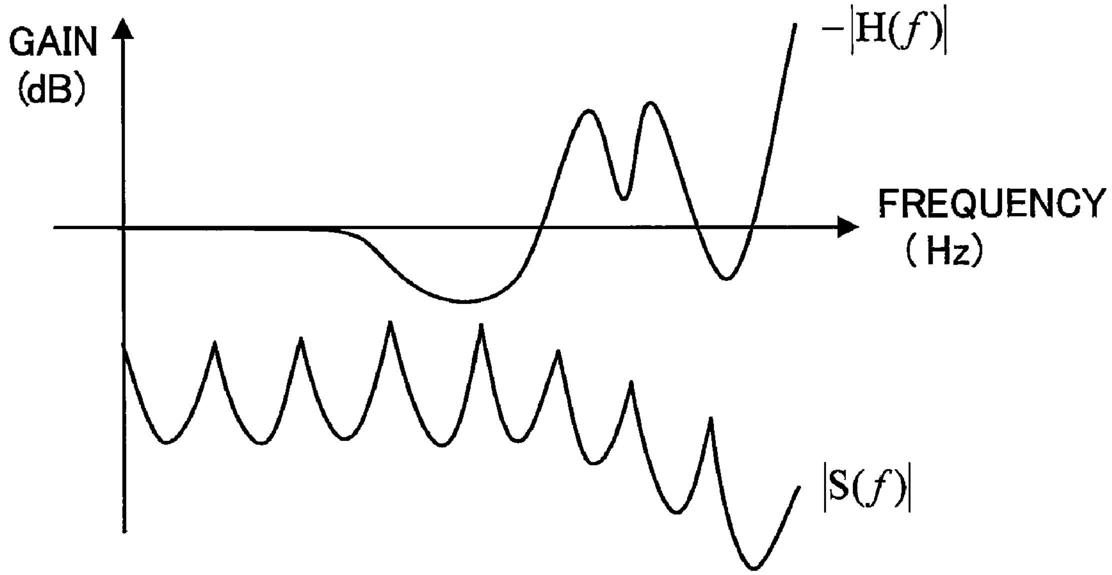
FIG. 2 is a diagram showing one example of comparative analysis between the sound source signal and the head-related transfer function.

As a concrete operation of the frequency component comparing/correcting unit 105, as shown in FIG. 2, it compares the amplitude component $|S(f)|$ which is the absolute value of the frequency component of the normalized sound source signal with the component $-|H(f)|$ which is the opposite sign of the absolute value of the amplitude component of the frequency component of the head-related transfer function.

When, for example, the selected head-related transfer function is convolved with the sound source signal under the condition that $-|H(f)|>|S(f)|$ over the entire frequency range, the sound image localizing signal is not distorted by the clipping distortion. Therefore, the frequency component comparing/correcting unit 105 outputs the selected head-related transfer function to the sound image localization processing unit 106 without correcting the selected head-related transfer function when $-|H(f)|>|S(f)|$ over the entire frequency range.

Figure 3:
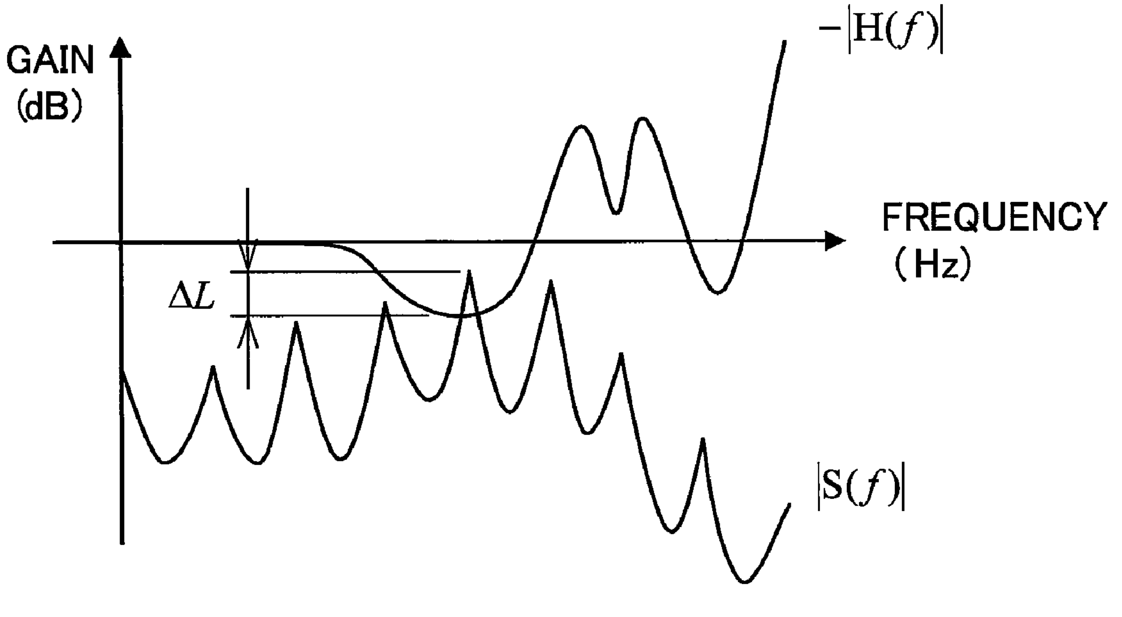
FIG. 3 is a diagram showing another example of comparative analysis between the sound source signal and the head-related transfer function.

When the selected head-related transfer function is convolved with the sound source signal under the condition that $-|H(f)|<|S(f)|$ in a frequency range as shown in FIG. 3, the sound image localizing signal is distorted by the clipping distortion. The frequency component comparing/correcting unit 105 corrects the selected head-related transfer function to ensure that $-|H(f)|>|S(f)|$ over the entire frequency range, and outputs the corrected head-related transfer function to the sound image localization processing unit 106. Therefore, the sound image localization apparatus can suppress a clipping distortion.

Figure 4:
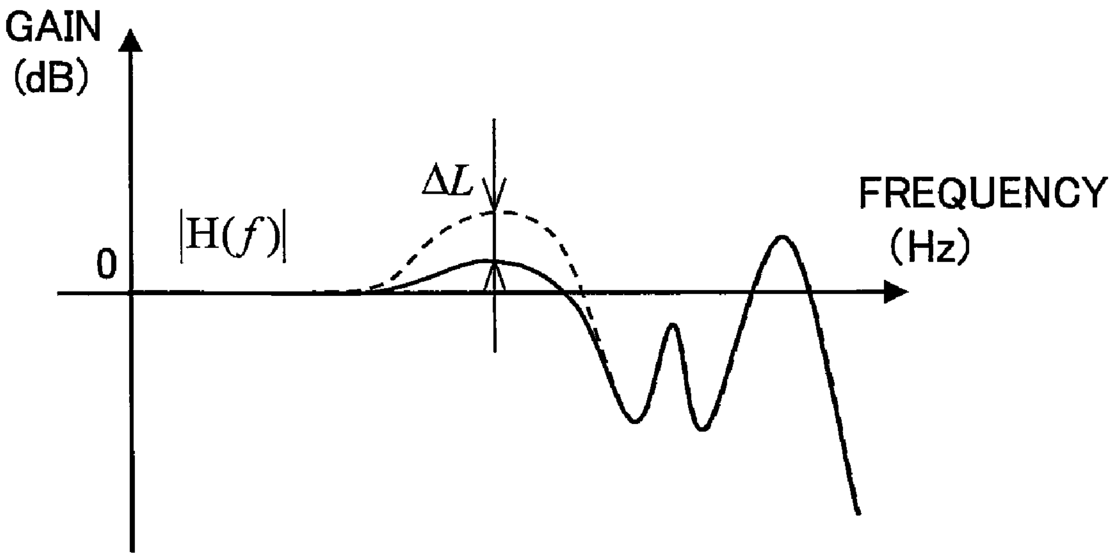
FIG. 4 is a diagram showing an example of correction for the head-related transfer function.

In this case, the deterioration of the sound image positioning component is prevented not only by correcting the frequency range which becomes $-|H(f)|>|S(f)|$, but by correcting the head-related transfer function H(f) so as to suppress the frequency component for each unit of peak including the above frequency range by a difference amount ΔL, as shown in FIG. 4.

Figure 5:
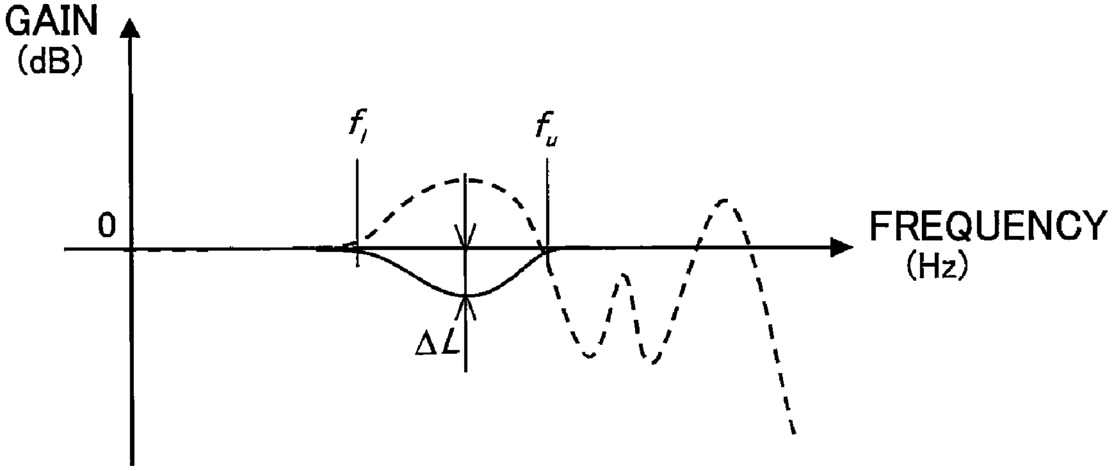
FIG. 5 is a diagram showing one example of IIR filter for performing correction for the head-related transfer function.
Figure 6:
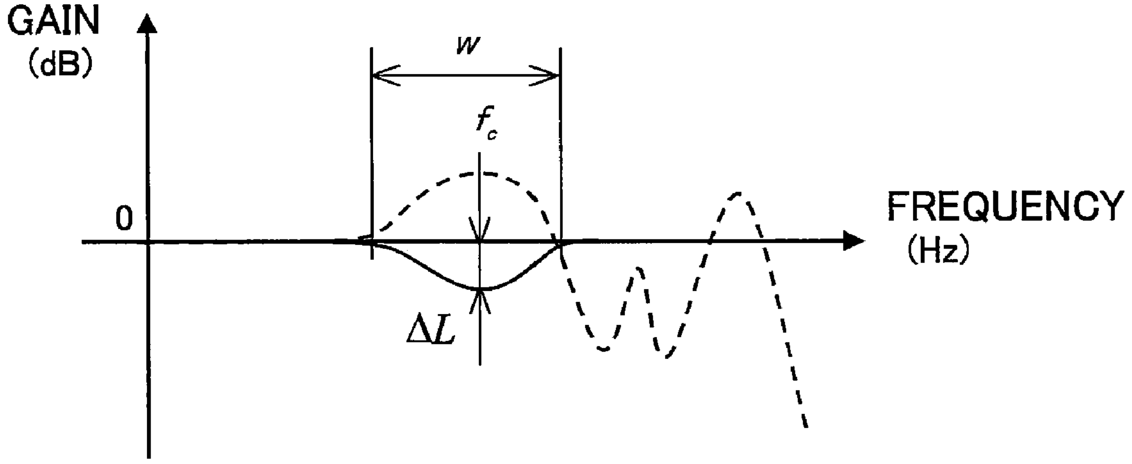
FIG. 6 is a diagram showing another example of IIR filter for performing correction for the head-related transfer function.
Figure 7:
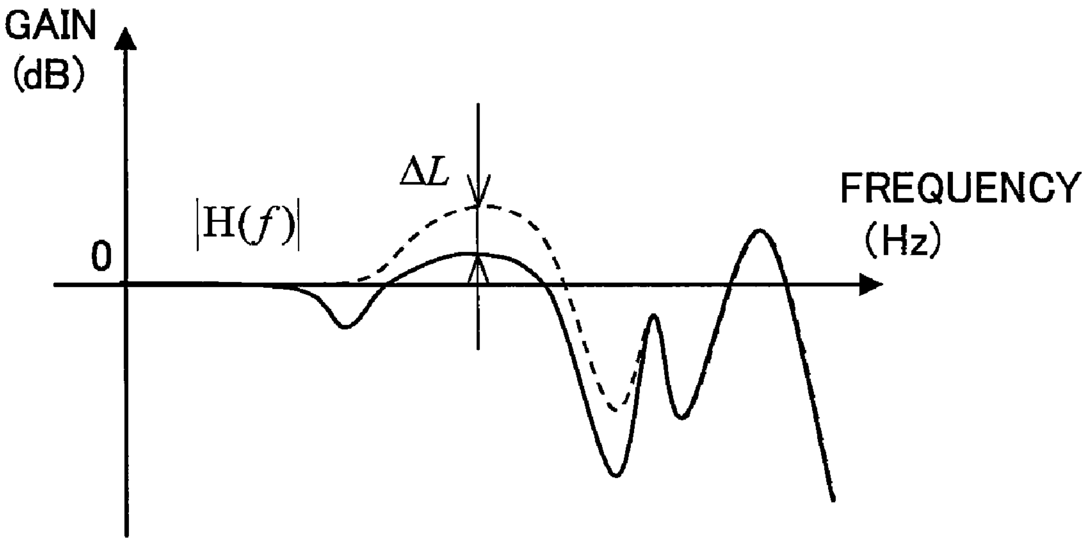
FIG. 7 is a diagram showing an example of correction for the head-related transfer function.

As a concrete example, the frequencies $f_1$ and $f_u$ defined on both side of the peak as shown in FIG. 5 may be prepared in advance as additional information, and attached to the head-related transfer function (HRTF) corresponding to the direction of the sound image, or may be automatically computed from the selected head-related transfer function (HRTF). Then, an IIR filter is constructed on the basis of the frequencies $f_1$ and $f_u$, and suppresses the frequency components of the head-related transfer function (HRTF) by a difference value ΔL in that frequency range.

Alternatively, the center frequency $f_c$ and the bandwidth w of the peak can be prepared in advance for each HRTF toward the positioning direction. Otherwise, these will be computed automatically from the given HRTF. Then, based on these frequency values, an IIR filter is constructed and applied to HRTF so that the frequency component where the clipping occurs is suppressed by an amount ΔL.

Also, the inventor showed that it is possible to position a sound image at a target location by suppressing the amplitude component of the frequency range corresponding to at least one side of the peak which occurs in the amplitude component of the head-related transfer function (see Japanese Patent Application 2004-270316).

Consequently, in addition to suppressing the peaks of the head-related transfer function H(f) as shown in FIG. 4, by emphasizing a dip on at least one of the sides of the peak frequency range, or by applying a signal correction to create a dip, it is possible to prevent the deterioration of the sound image localization component of the sound image localizing signal even though the peak is suppressed, and to further prevent the clipping.

Figure 8:
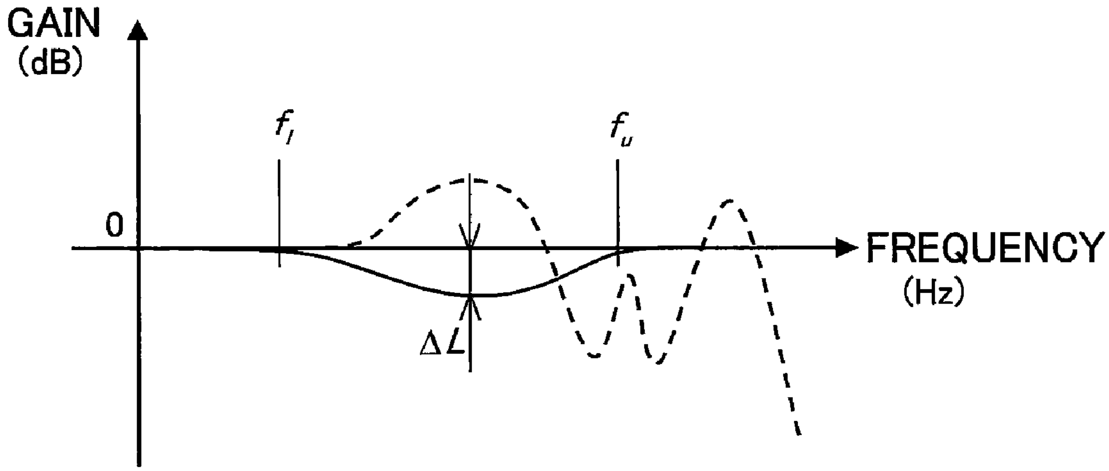
FIG. 8 is a diagram showing an example of IIR filter for performing a correction for the head-related transfer function.
Figure 9:
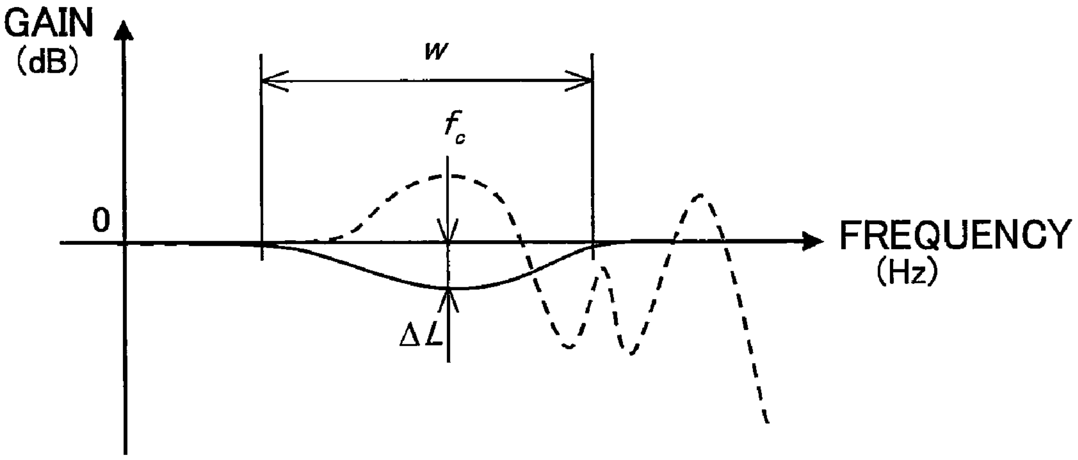
FIG. 9 is a diagram showing an example of IIR filter for performing a correction for the head-related transfer function.

As a concrete example, as shown in FIG. 8, the frequencies of the created dip or dips on the lower and the upper sides of the peak are set to $f_1$ and $f_u$, and prepared in advance as additional information to HRTF of the positioning direction. Otherwise, this information is computed from the given HRTF automatically. Then, based on these frequency values, an IIR filter is constructed and applied to HRTF in the way so that the frequency component where the clipping occurs is suppressed by an amount ΔL.

Alternatively, the center frequency $f_c$ and the bandwidth w can be prepared in advance for each HRTF in the positioning direction and set to cover over the dips on both sides of the peak or the dips to be created. Otherwise, these will be computed automatically from the given HRTF. Then, based on these frequency values, an IIR filter is constructed and applied to HRTF so that the frequency component where the clipping occurs is suppressed by an amount ΔL.

Figure 10:
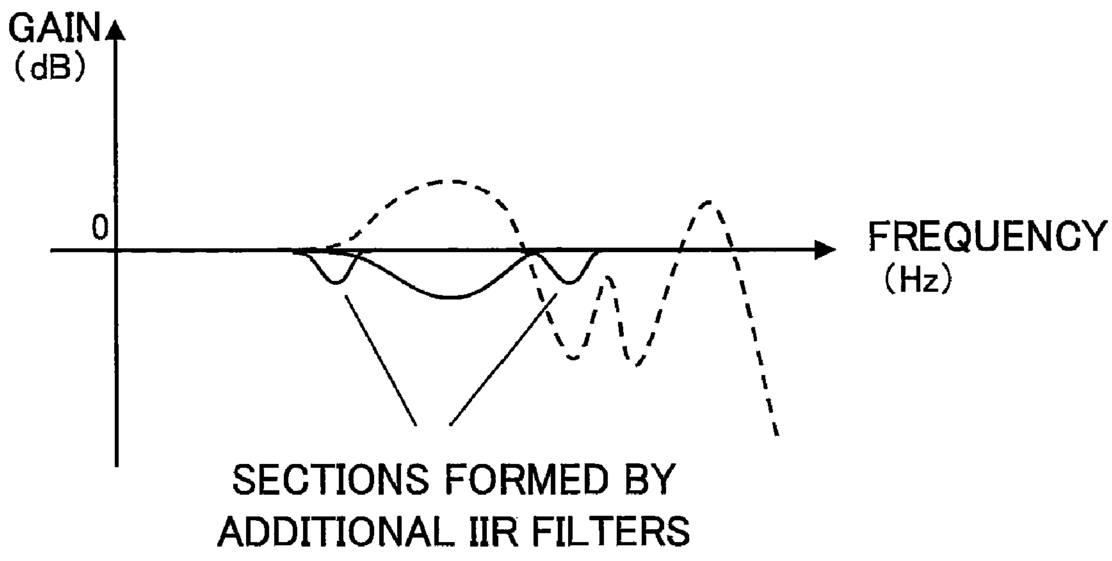
FIG. 10 is a diagram showing an example of IIR filter for performing a correction for the head-related transfer function.

In both cases, if the dip on both sides of the peak cannot be emphasized enough, or if it is not possible to create a new dip, an IIR filter can be added to the relevant range as shown in FIG. 10.

The sound image localization processing unit 106 multiplies the frequency component of the sound source signal with the frequency component of the head-related transfer function, which corresponds to the convolution in the time domain, and outputs the sound image localizing signal which is converted, using inverse Fourier transform, into time domain waveform.

As explained above, in the first embodiment of the present invention, the sound image localization is processed by comparing the frequency component of the sound source signal with that of the head-related transfer function and by correcting, for each unit of peak or dip, the head-related transfer function over the frequency component where the clipping occurs and its neighboring frequency component. These processes can prevent the volume decrease of the sound image localizing signal and clipping, and avoid the deterioration of the sound image positioning component of the sound image localizing signal.

Also, in the first embodiment of the present invention, although the frequency component comparing/correcting unit 105 suppresses the clipping distortion by correcting the head-related transfer function, it is possible to achieve the same effect by correcting the sound source signal.

Figure 11:
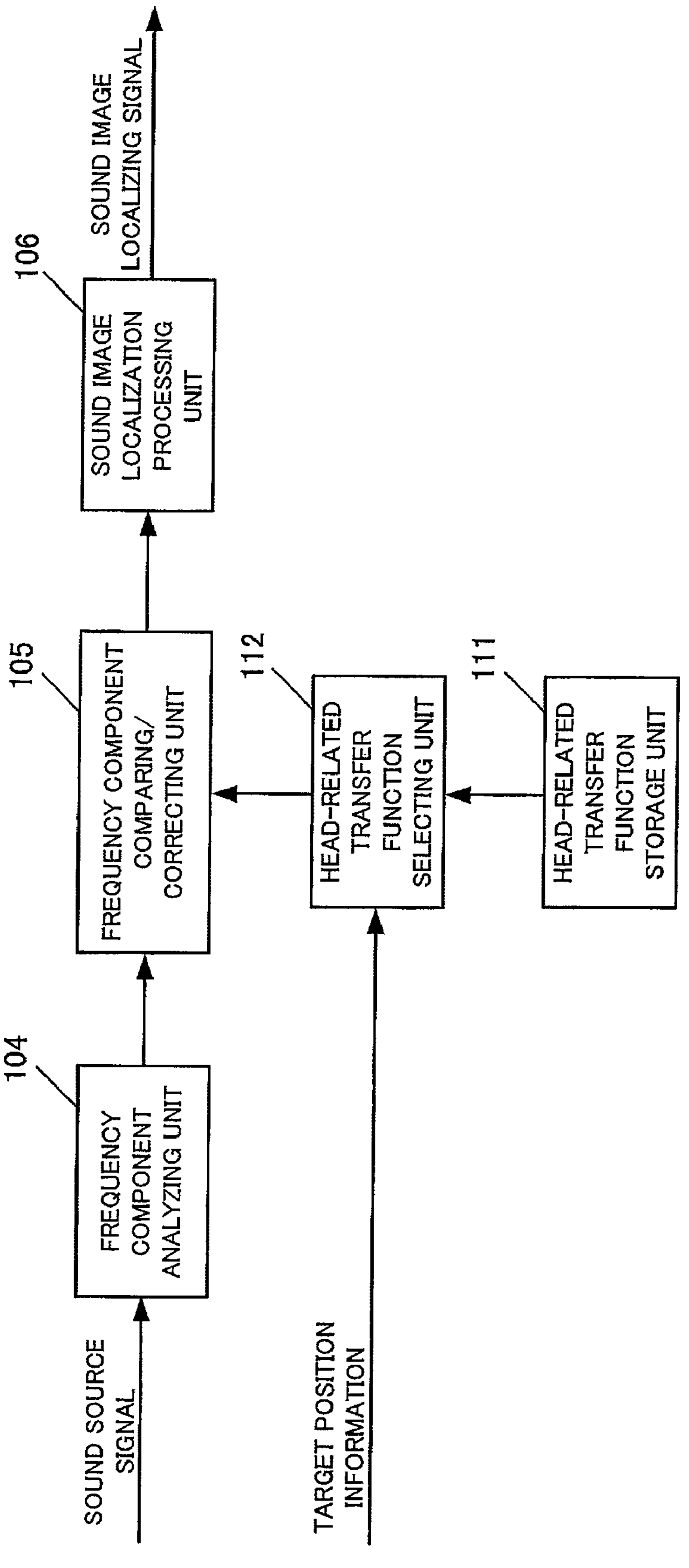
FIG. 11 is a block diagram of a modification of the first embodiment of the sound image localization apparatus according to the present invention.

As a modification of the first embodiment of the invention, instead of the structure explained in FIG. 1, as shown in FIG. 11, a head-related transfer function storage section 111 can store the head-related transfer function converted into the frequency components by the Fourier transform from the beginning instead of the FIR (Finite Impulse Response) filter coefficient, and a head-related transfer function selecting section 112 is made to select and output the head-related transfer function stored in the head-related transfer function storage section 111 according to the inputted target position information. By structuring in this way, the frequency analysis of the head-related transfer function as explained in FIG. 1 can be omitted so that sound image positioning can be performed with smaller amount of calculation.

Figure 12:
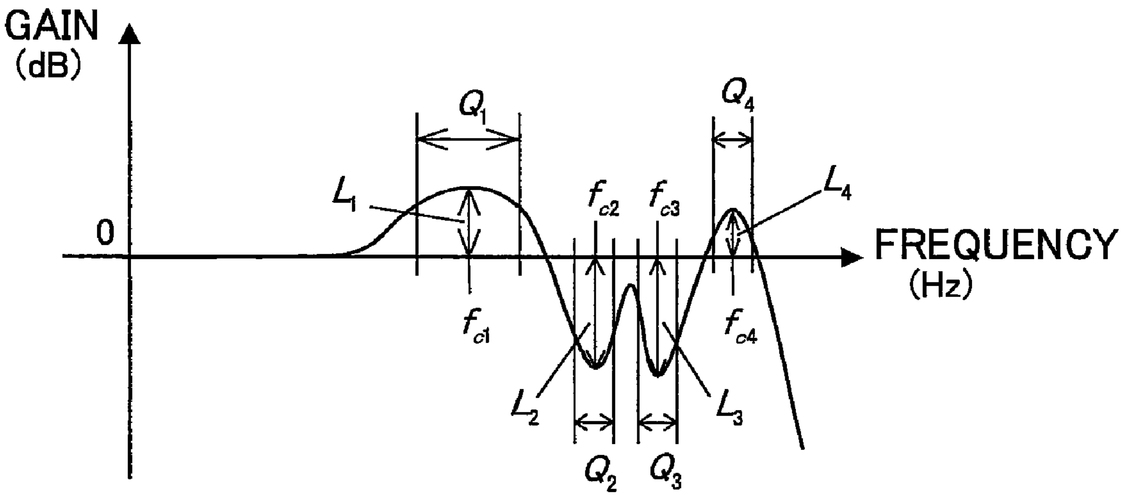
FIG. 12 is a diagram showing an example of bi-quad type IIR filter.

As another modification of the first embodiment of the present invention, the head-related transfer function may be generated by a plurality of IIR filters as shown in FIG. 12. In FIG. 12, the head-related transfer function is generated by a plurality of biquad IIR filters. The head-related transfer function may be generated by other type of IIR filters.

As explained with reference to FIG. 1, the head-related transfer function storage unit 101 has parameters of each Infinite Impulse Response filter (IIR filter), i.e., center frequency $f_c$, level L, and sharpness Q of each IIR filter. The frequency component analyzing unit 103 analyzes the head-related transfer function selected by the head-related transfer function selecting unit 102.

Figure 13:
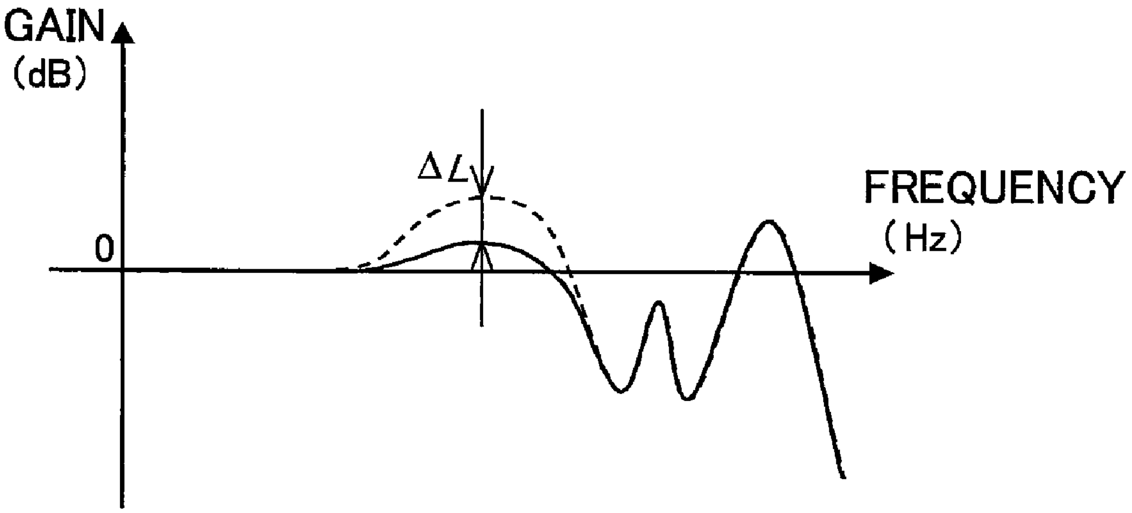
FIG. 13 is a diagram showing another example of bi-quad type IIR filter.

As shown in FIG. 2 or FIG. 3, the frequency component comparing/correcting unit 105 compares the frequency component of the selected head-related transfer function with the frequency component of the sound source signal. When the determination is made that the sound image localizing signal is distorted by the clipping distortion, the frequency component comparing/correcting unit 105 suppresses, by ΔL, the level L of the IIR filter corresponding to a relevant peak as shown in FIG. 13.

Figure 14:
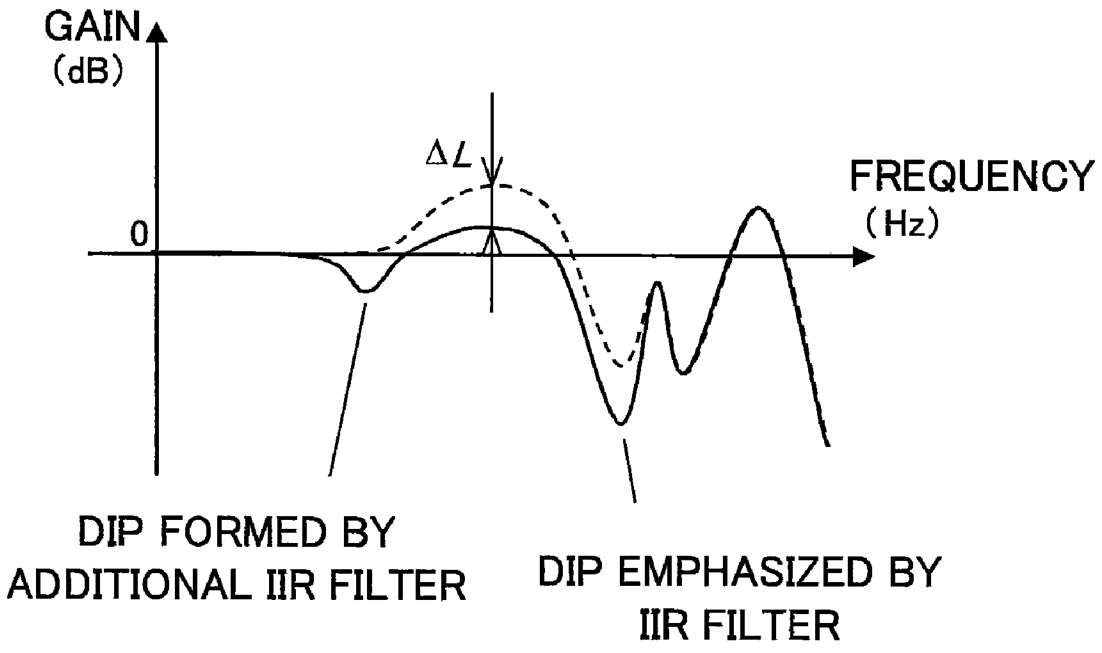
FIG. 14 is a diagram showing a further example of bi-quad type IIR filter.

As shown in FIG. 14, the frequency component comparing/correcting unit 105 may suppress a level L of the IIR filter corresponding to a relevant peak, and emphasize dips on both sides of the peak by correcting parameters of the IIR filter. In order to create a new dip, the number of the IIR filters may be increased.

The sound image localization processing unit 106 outputs a sound image localizing signal by filtering the sound source signal on the basis of the corrected parameters of the IIR filters.

The sound image localization apparatus thus constructed can perform a sound image localizing operation with a small number of calculations for the sound image localizing operation in comparison with FIR filters.

Second Embodiment

Figure 15:
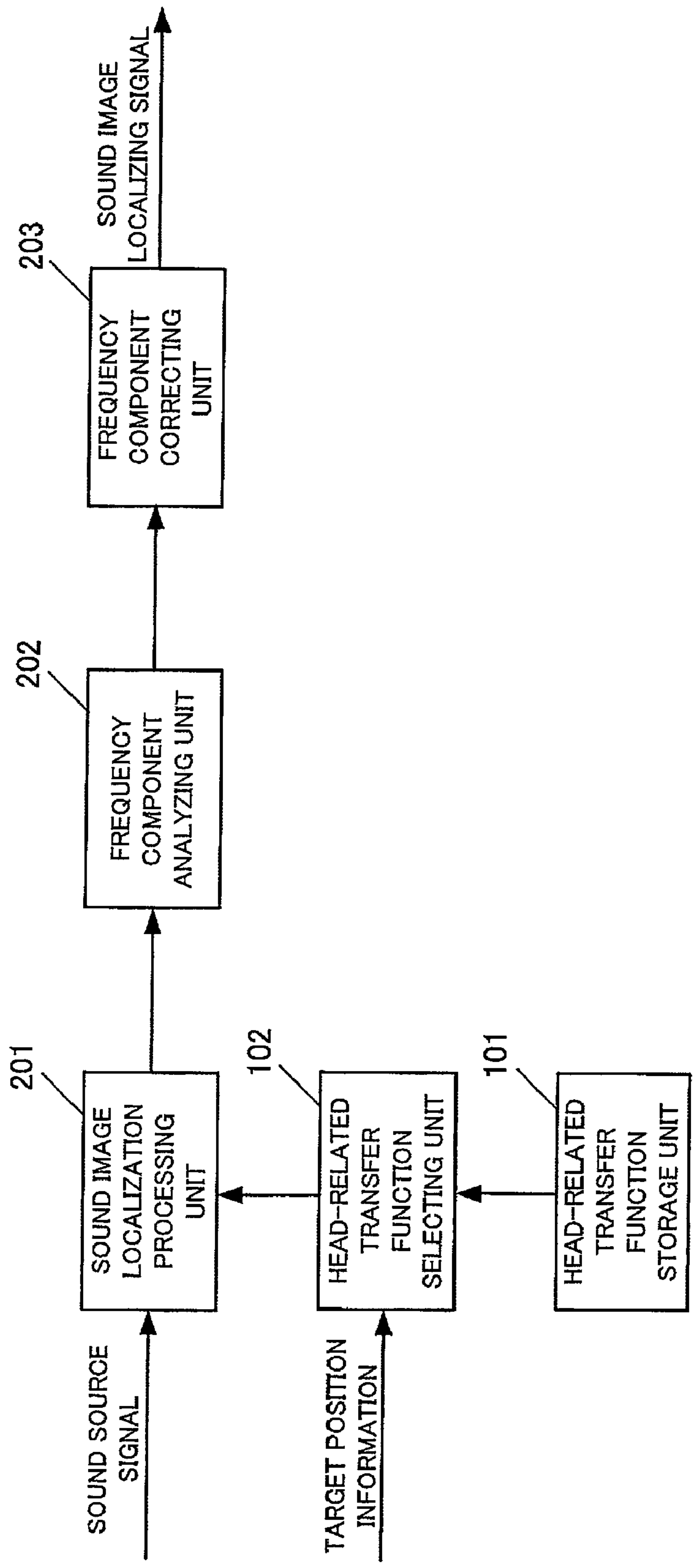
FIG. 15 is a block diagram showing a sound image localization apparatus according to the second embodiment of the present invention.

FIG. 15 is a block diagram showing a sound image localization apparatus according to the second embodiment of the present invention.

As shown in FIG. 15, the sound image localization apparatus comprises a head-related transfer function storage unit 101 having head-related transfer functions corresponding to respective positions, a head-related transfer function selecting unit 102 operable to select a head-related transfer function on the basis of information on a position at which a sound image is localized, a sound image localization processing unit 201 operable to applies a filter onto the input sound-signal based on the head-related transfer function and performs the sound image localization processing, a frequency component analyzing unit 202 operable to analyze frequency components of sound image localizing signal processed by the sound image localization processing unit 201, and a frequency component correcting unit 203 correcting the frequency component in case the clipping occurs in the sound image localizing signal.

Also, the same numerical references are applied to components of the sound image localization apparatus related to the second embodiment of the present invention which are the same as that used for the sound image localization apparatus related to the first embodiment.

The following description is directed to the operation of the sound image localization apparatus according to the second embodiment of the present invention.

As shown in FIG. 15, the sound image processing unit 201 performs convolution of a sound source signal and a head-related transfer function selected by the head-related transfer function selecting unit 102, and outputs a sound image localizing signal to the frequency component analyzing unit 202 as an output signal. In order to suppress a clipping distortion, output signal range must be taken to be sufficiently large. For example, if the sound image localization processing unit 201 performs a digital signal processing, and if the output signal exceeds 16 bits, the output signal must be represented by an integer larger than 16 bits or a floating point representation must be used.

The frequency component analyzing unit 202 converts a sound image localizing signal computationally generated by the sound image localization processing unit 201 into frequency components by using Fourier transform method or the like, and outputs the frequency components to the frequency component correcting unit 203.

The frequency component correcting unit 203 determines whether the clipping has occurred in a particular frequency range or not, and if the clipping is determined to have occurred, the correction of the sound image localizing signal is performed on each unit of the peaks or the dips of the head-related transfer function by preparing the frequencies in advance on either sides of the peak of the head-related transfer function similarly to the frequency component comparing/correcting unit 105 as discussed in the first embodiment or by computing these frequencies automatically. Then, it outputs the sound image localizing signal which is converted, using inverse Fourier transform, into time domain waveform.

Figure 16:
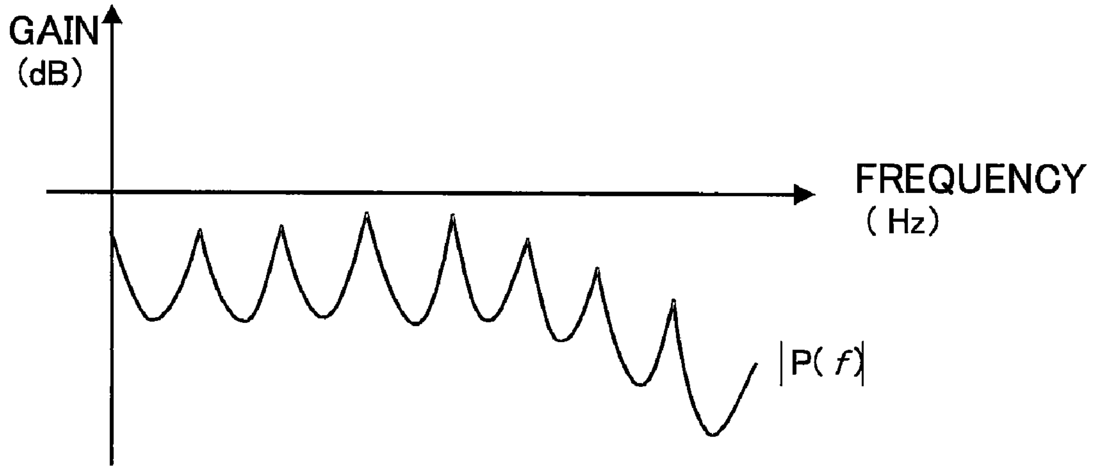
FIG. 16 is a diagram showing an example of the determination on whether the sound image localizing signal is distorted by the clipping distortion in the sound image localization apparatus according to the second embodiment of the present invention.

When, for example, the absolute value |P(f)| of the amplitude component of the sound image localizing signal does not exceed 0 dB over the entire frequency range as shown in FIG. 16, the determination is made that the sound image localizing signal is not distorted by the clipping distortion.

Figure 17:
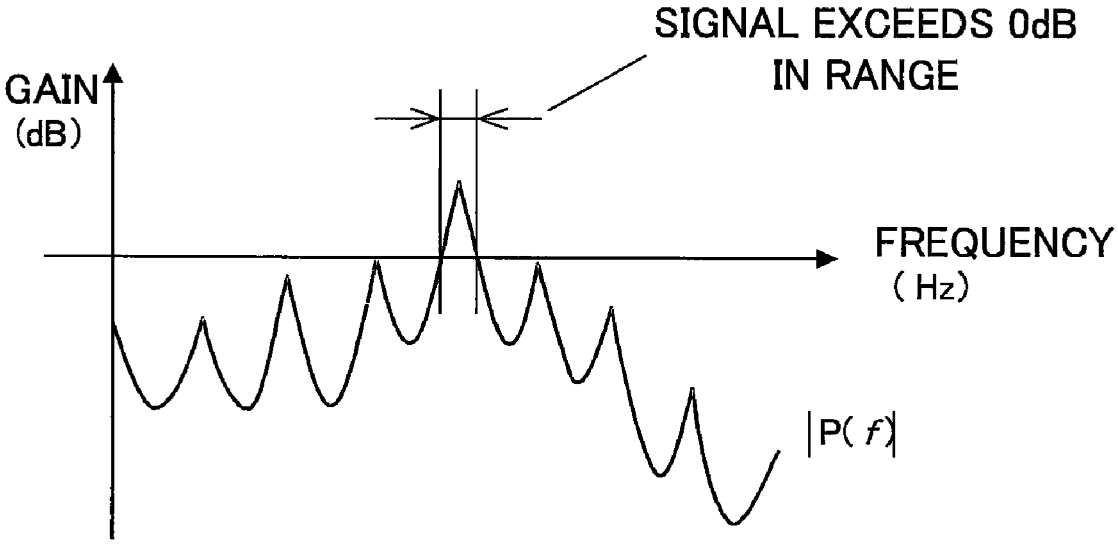
FIG. 17 is a diagram showing an example of the determination on whether the sound image localizing signal is distorted by the clipping distortion in the sound image localization apparatus according to the second embodiment in the present invention.

As shown in FIG. 17, when the absolute value |P(f)| of the amplitude component of the sound image localizing signal exceeds 0 dB in a frequency range, the determination is made that the sound image localizing signal is being distorted in this frequency range.

As explained above, in the second embodiment of the invention, the sound source signal is convolved with the head-related transfer function, and only the amplitude component of the convolved sound source signal corresponding to the frequency range in which the clipping occurs and its neighboring frequency ranges is suppressed and output. This suppression prevents the volume of the sound image localizing signal from decreasing and clipping, and then avoids the deterioration of the sound image positioning component of the sound image localizing signal.

Figure 18:
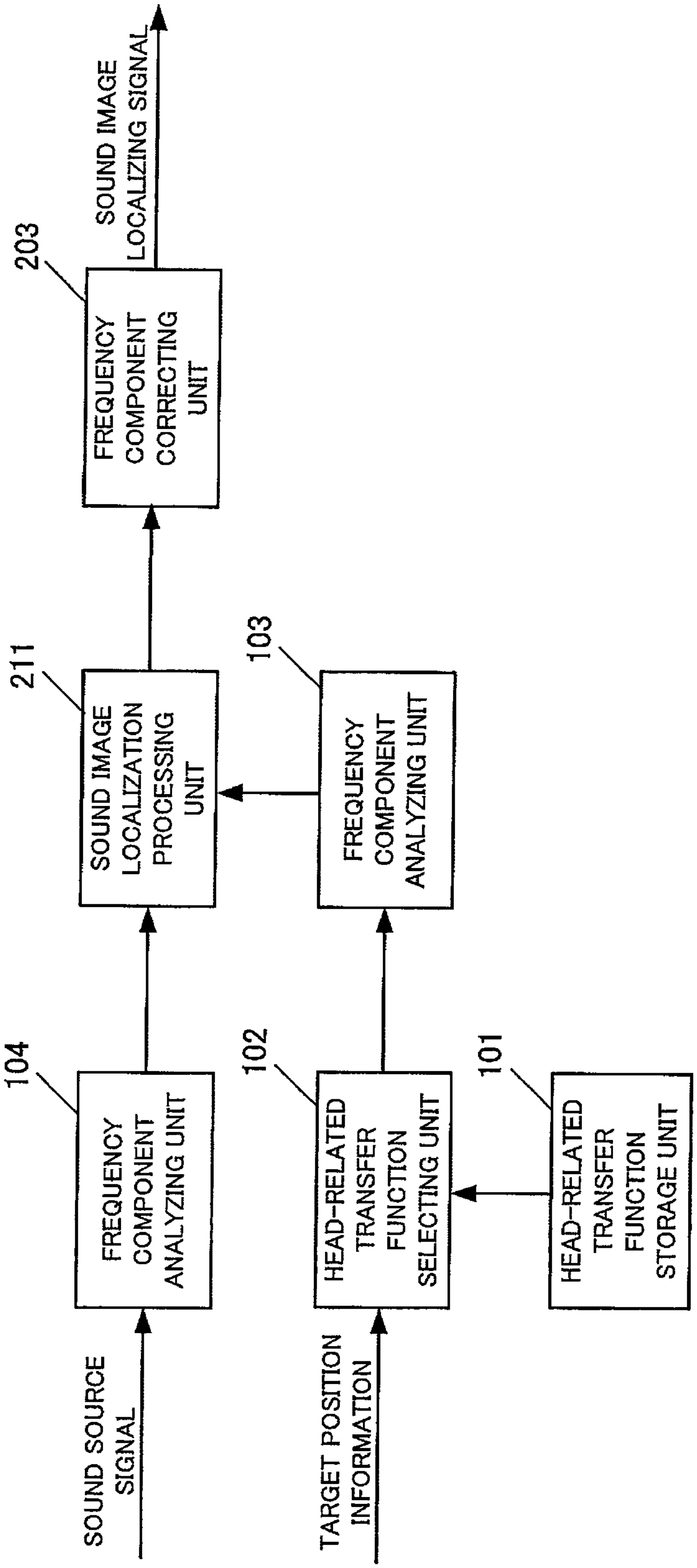
FIG. 18 is a block diagram showing the first alternate form of the sound image localization apparatus according to the second embodiment of the present invention.

As shown in FIG. 18, in a modification of the second embodiment of the present invention, the sound image localization processing unit 201 and the frequency component analyzing unit 202 explained in the second embodiment may be replaced with a sound image localization processing unit 211 and frequency component analyzing units 103 and 104. In this modification, the sound image localization apparatus is operative to multiply the frequency component of the sound source signal with the frequency component of the head-related transfer function in the frequency domain as an operation corresponding to the convolution to be performed in the time domain.

Figure 19:
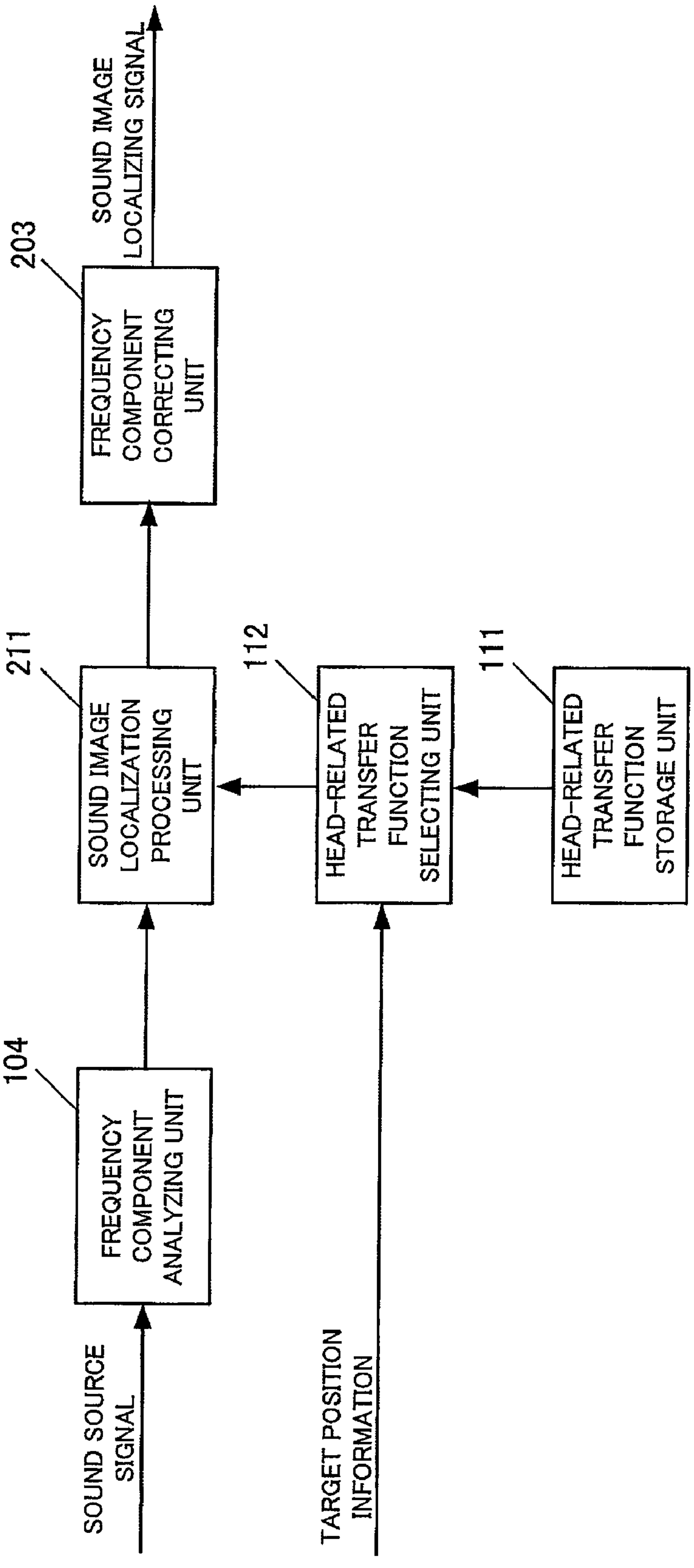
FIG. 19 is a block diagram showing the second alternate form of the sound image localization apparatus according to the second embodiment of the present invention.
Figure 20:
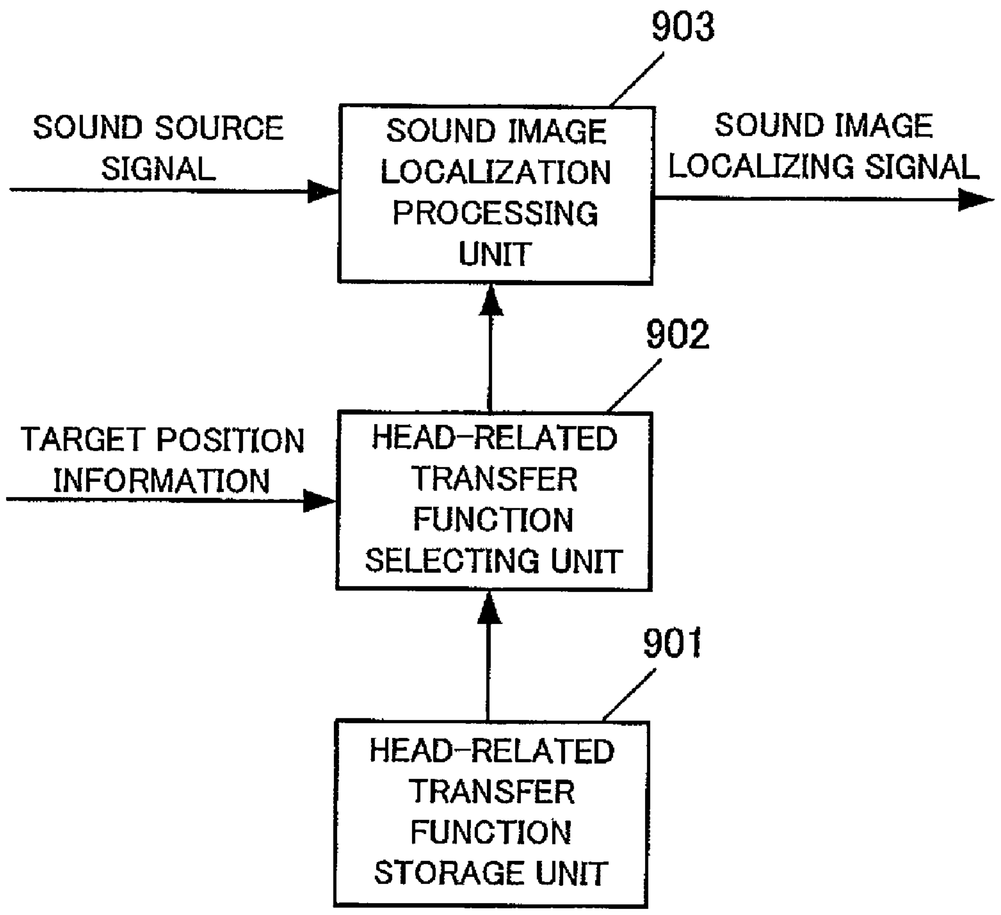
FIG. 20 PRIOR ART
FIG. 20 is a block diagram showing the conventional sound image localization apparatus.

Also, as shown in FIG. 19, in another modification of the second embodiment of the present invention, the head-related transfer function storage unit 101, the head-related transfer function selecting unit 102, and the frequency component analyzing unit 103 shown in FIG. 18 may be replaced with a head-related transfer function storage unit 111 and a head-related transfer function selecting unit 112. In this modification, the sound image localization apparatus is operative to perform sound image localizing operation by using previously-transformed frequency component of the head-related transfer function.

In each embodiment, if the sound image localization apparatus can estimate a frequency range in which the sound image localizing signal is distorted, the sound image localization apparatus may be operative to determine whether or not the sound image localizing signal is distorted only in a frequency range previously estimated, and can obtain the same advantageous effects.

For example, as shown in FIG. 21, because clipping cannot possibly occur in the frequency range in which the head-related transfer function's gain does not exceed 0 dB, the same effect can be achieved by restricting the frequency range in which the clipping is determined to those frequency ranges where the gain of the head-related transfer function exceeds 0 dB. Consequently, the number of calculation related to sound image positioning can be decreased.

Also, the time length during which the frequency component analyzer 103 converts the sound source signal or the head-related transfer function into frequency components may be set to be the same length as the inputted sound source signal or it may be set shorter.

When using the limiter and the compressor in each of the aforementioned embodiment as used in the existing sound image localization apparatus, the amount of suppression applied to the amplitude component corresponding to the frequency range on which the clipping occurs can be set slightly less. This process decreases the nonlinear transformation of the frequency component that arises due to the processing of the limiter and compressor; therefore, the deterioration of the component used for the sound image localization in the sound image localizing signal is prevented.

According to "Spatial Hearing" by Blauert (Kajima Institute Publishing), it has been found that there is a deep connection between the sound image localization and an auditory phenomenon called "directional band."

For example, in case the clipping peak coincides with the directional band of the target direction, a dip may be emphasized or created on either sides of the peak in addition to suppressing the peak as it is an important component of the sound image localization. On the other hand, if the peak does not coincide with the directional band of the target direction, the peak may simply be suppressed due to the fact that it is not an important component of the sound image localization.

Thus, in the above, the explanation of the first and second embodiments has been given. It should be noted that because the sound image localization apparatus related to the embodiments of the present invention memorizes the head-related transfer function as a data of the frequency component using the head-related transfer function storage section 111, the frequency analysis of the head-related transfer function is omitted. Therefore, the sound image localization can be realized with smaller amount of calculation.

Additionally, the sound image localization apparatus according to the first and second embodiments of the present invention can limit the frequency range from which the occurrence of clipping is determined due to the fact that the clipping is determined only for the frequency range whose amplitude of the frequency component of the head-related transfer function exceeds predetermined amplitude such as 0 dB. Therefore, sound image localization can be realized with smaller amount of calculation.

INDUSTRIAL APPLICABILITY OF THE INVENTION

As will be seen from the foregoing description, the sound image localization apparatus according to the present invention can suppress a clipping distortion without reducing the volume of the sound image localizing signal, and prevent its signal components necessary for localizing a sound image from being deteriorated. Thus, it has considerable applicability for general devices that plays sound such as cellular phones that use sound image localization, sound devices, sound recorders, communication devices, game devices, conference devices, communication and broadcasting systems.

The invention claimed is:

1. A sound image localization apparatus for executing a sound image localizing processing on the basis of a head-related transfer function, comprising:

a frequency component comparing/correcting unit operable to compare frequency components of a sound source signal with frequency components of said head-related transfer function corresponding to a position of said sound image to be localized, to determine whether or not a sound image localizing signal is distorted by a clipping distortion, and to correct said frequency components of said head-related transfer function when said sound image localizing signal is distorted by said clipping distortion; and a sound image localization processing unit operable to execute data processing by using said sound source signal and said head-related transfer function corrected by said frequency component comparing/correcting unit, to output a sound image localizing signal, wherein said frequency component comparing/correcting unit suppresses an amplitude of said head-related transfer function for each unit of peak or dip.

2. The sound image localization apparatus according to claim 1, wherein said frequency component comparing/correcting unit corrects said frequency components of said head-related transfer function to suppress said amplitude of said head-related transfer function for each unit of peak, and to create a new dip around a peak.

3. The sound image localization apparatus according to claim 1 or claim 2, further comprising a head-related transfer function storage unit having data on frequency components of head-related transfer functions.

4. The sound image localization apparatus according to claim 1 or claim 2, wherein said frequency component comparing/correcting unit determines whether or not said sound image localizing signal is distorted by a clipping distortion only in a frequency range where said amplitude of said head-related transfer function exceeds a predetermined value.

5. The sound image localization apparatus according to claim 4, wherein said predetermined value is 0 dB.

6. The sound image localization apparatus according to claim 1 or claim 2, wherein a method of suppressing said amplitude component is changed on the basis of a determination on whether said frequency region where said clipping distortion does occur is a directional band or not.

* * * * *